United States Patent [19]
Levings, III et al.

[11] Patent Number: 5,665,349
[45] Date of Patent: Sep. 9, 1997

[54] RECOMBINANT BACULOVIRUS WITH INSECTICIDAL ACTIVITY

[75] Inventors: Charles S. Levings, III, Raleigh, N.C.; Kenneth L. Korth, Ardmore, Okla.

[73] Assignee: North Carolina State University, Raleigh, N.C.

[21] Appl. No.: 533,215

[22] Filed: Sep. 22, 1995

Related U.S. Application Data

[63] Continuation of Ser. No. 139,440, Oct. 20, 1993, abandoned.

[51] Int. Cl.$^6$ .................. A01N 63/00; C12N 7/01; C12N 15/29; C12N 15/34; C12N 15/86
[52] U.S. Cl. .............. 424/93.2; 424/93.6; 435/69.1; 435/69.7; 435/71.1; 435/172.3; 435/235.1; 435/320.1; 536/23.6; 536/23.72; 536/24.1
[58] Field of Search .................. 424/93.2, 93.6; 435/69.1, 69.7, 71.1, 172.3, 235.1, 320.1; 536/23.6, 23.72, 24.1

[56] References Cited

U.S. PATENT DOCUMENTS

| | | | |
|---|---|---|---|
| 4,745,051 | 5/1988 | Smith et al. | 435/69.1 |
| 4,870,023 | 9/1989 | Fraser et al. | 435/320.1 |
| 4,879,236 | 11/1989 | Smith et al. | 435/235.1 |
| 5,071,748 | 12/1991 | Miller | 435/69.1 |
| 5,229,112 | 7/1993 | Obakowicz et al. | 424/93 A |

OTHER PUBLICATIONS

C. J. Braun et al., Mutations in the maize mitochondrial T–urf13 gene eliminate sensitivity to a fungal pathotoxin, *Proc. Natl. Acad. Sci.* 86, 4435–4439 (1989).
C.J. Braun et al., Fungal Toxins Bind to the URF13 Protein in Maize Mitochondria and *Escherichia coli*, *The Plant Cell*, 2, 153–161 (1990).
J. Huang et al., Expression in yeast of the T–URF13 protein from Texas male–sterile maize mitochondria confers sensitivity to methomyl and to Texas–cytopolasm–specific fungal toxins, *The EMBO Journal* 9, 339–347 (1990).
K.L. Korth et al., URF13, a maize mitochondrial pore–forming protein, is oligomeric and has a mixed orientation in *Escherichia coli* plasma membranes, *Proc. Natl. Acad. Sci.* 88, 10865–10869 (1991).
Luckow, V. 1995. Baculovirus Expression Systems and Biopesticides, pp. 51–90, Wiley–Liss, Inc.
Cory et al. 1994. Nature 370: 138–140.
Smith et al. 1983. Mol. Cell. Biol. 3(12): 2156–2165.
Pennock et al. 1984. Mol. Cell. Biol. 4(3): 399–406.
Wood, H. 1995. Baculovirus Expression Systems and Biopesticides, pp. 91–102, Wiley–Liss, Inc.
Bishop et al. 1990. New Directions in Biological Control: Alternatives for Suppresing Agricultural Pests and Diseases, pp. 609–628, Alan R. Liss, Inc.
Jacques, R. 1975. pp. 90–101 In: Baculoviruses for Insect Pest Control: Safety Considerations, Summers/et al. (eds.), Am. Soc. Microbiol.
Korth et al. 1993. Proc. Natl. Acad. Sci. USA 90: 3388–3392.
Lewin, R. 1987. Science 237: 1570.
Reeck et al. 1987. Cell 50: 667.
Yamada et al. 1990. Biochem J. 272: 633–636.
Purcell et al. 1992. Insect Biochem. Molec. Biol. 22(1): 41–47.

*Primary Examiner*—David T. Fox
*Attorney, Agent, or Firm*—Bell, Seltzer, Park & Gibson

[57] ABSTRACT

A method of agricultural pest control using recombinant baculovirus which express DNA coding for the mitochondrial pore-forming protein URF13, or homologous DNA. Compositions for agricultural use containing the recombinant baculovirus.

34 Claims, 1 Drawing Sheet

RECOMBINANT BACULOVIRUS WITH INSECTICIDAL ACTIVITY

This is a continuation of application Ser. No. 08/139,440 filed on 20 Oct. 1993, now abandoned.

This invention was made with government support under Grant No. DMD-88-12916 awarded by the National Science Foundation. The government has certain rights in the invention.

FIELD OF THE INVENTION

This invention relates to methods of controlling agricultural insect pests generally, and particularly relates to a method of controlling insect pests using a recombinant baculovirus which expresses a maize mitochondrial protein. The invention further relates to agricultural compositions for use in these methods.

BACKGROUND OF THE INVENTION

The mitochondrial gene T-urf13 is found in maize with Texas male-sterile cytoplasm (cms-T), and encodes a maize mitochondrial protein. The DNA encoding URF13 (T-urf13) is thought to have arisen by multiple derived from four different origins. See Dewey et al., *Cell*, 44, 439 (1986). In maize the URF13 protein causes susceptibility to toxins produced by two fungal pathogens, *Bipolaris maydis* race T (formerly *Helminthosporium maydis* race T) and *Phyllosticta maydis*. Diseases caused by these pathogens have curtailed large-scale use of cms-T maize for the production of hybrid seed. Treating isolated cms-T maize mitochondria with the host-specific fungal toxins (T toxins) produced by *B. maydis* race T (BmT toxin) or *P. maydis* (Pm toxin) causes mitochondrial swelling, leakage of small molecules and ions, inhibition of malate-stimulated respiration, and uncoupling of oxidative phosphorylation. BmT and Pm have been purified and characterized. See Kono et al., *Tetrahedron Lett.*, 24. 3803 (1983); Kono et al., *Bioorg. Chem.*, 10, 206 (1981); Kono et al., *Tetrahedron Lett.*, 21, 1537 (1981).

The interaction of URF13 and T toxin results in pore formation in the inner mitochondrial membrane, which causes membrane permeability. See Levings, *Science* 250, 942 (1990). Similar events are observed in *Escherichia coil* (*E. coli*) expressing the cloned T-urf13 gene where, after exposure to T toxins, spheroplast swelling, inhibition of respiration, and ion leakage occur. R. Dewey, et al., *Science* 239, 293 (1988); C. Braun, et al., *Proc. Natl. Acad. Sci. USA* 86, 4435 (1989); C. Braun et al., *Plant Cell*, 2, 153 (1990). Methomyl (S-methyl-N-[(methylcarbamoyl)oxy] thioacetimidate), the active ingredient in the DuPont insecticide LANNATE (TM), mimics the effects of T toxins on isolated cms-T maize mitochondria or *E. coli* expressing URF13. Dewey et al, *Science*, 239, 293 (1988); Koeppe et al, *Science*, 201, 1227 (1978). Many mutations in T-urf13, including several at nucleotide positions encoding amino acid residue 39, render *E. coli* expressing the mutant URF13 insensitive to T toxins or methomyl. Braun et al, *Proc. Natl. Acad. Sci. USA* 86, 4435 (1989); Mark E. Williams and Gerty C. Ward, personal communication.

URF13 has also been expressed in two heterologous eukaryotic systems. The T-urf13 gene was expressed in *Saccharomyces cerevisiae* where the gene was modified to direct URF13 import into mitochondria (Glab et al., *Mol. Gen. Genet.*, 223, 24 (1990); Huang et al., *EMBO J.*, 9, 339 (1990). In these cases URF13 accorded T toxin and methomyl sensitivity to the mitochondria. In contrast, when the URF13 protein was not modified to direct import into the mitochondria, it did not confer toxin sensitivity to whole yeast cells. URF13 conferred T toxin sensitivity to *Nicotiana tabacum*, however, when it was expressed in the cytoplasm without a mitochondrial targeting sequence. Von Allmen, et al., *Mol. Gen. Genet.* 229, 405 (1991).

SUMMARY OF THE INVENTION

A method of reducing the population of an insect in an agricultural field is disclosed. The method comprises applying to the field a recombinant baculovirus which is able to infect the insect and which contains and expresses a heterologous DNA selected from the group consisting of (a) isolated DNA which encodes the maize mitochondrial pore-forming protein URF13; (b) isolated DNA which is at least 75% homologous to the DNA of (a) above, and which hybridizes to isolated DNA of (a) above, and which encodes a membrane protein; and (c) isolated DNA differing from the isolated DNAs of (a) and (b) above in codon sequence due to the degeneracy of the genetic code. The recombinant baculovirus is applied in an amount effective to reduce the population of the insect.

Also disclosed are agricultural compositions useful in the above method. The compositions comprise the recombinant baculovirus, as above, and may comprise additional optional ingredients.

DETAILED DESCRIPTION OF THE INVENTION

Figure 1:
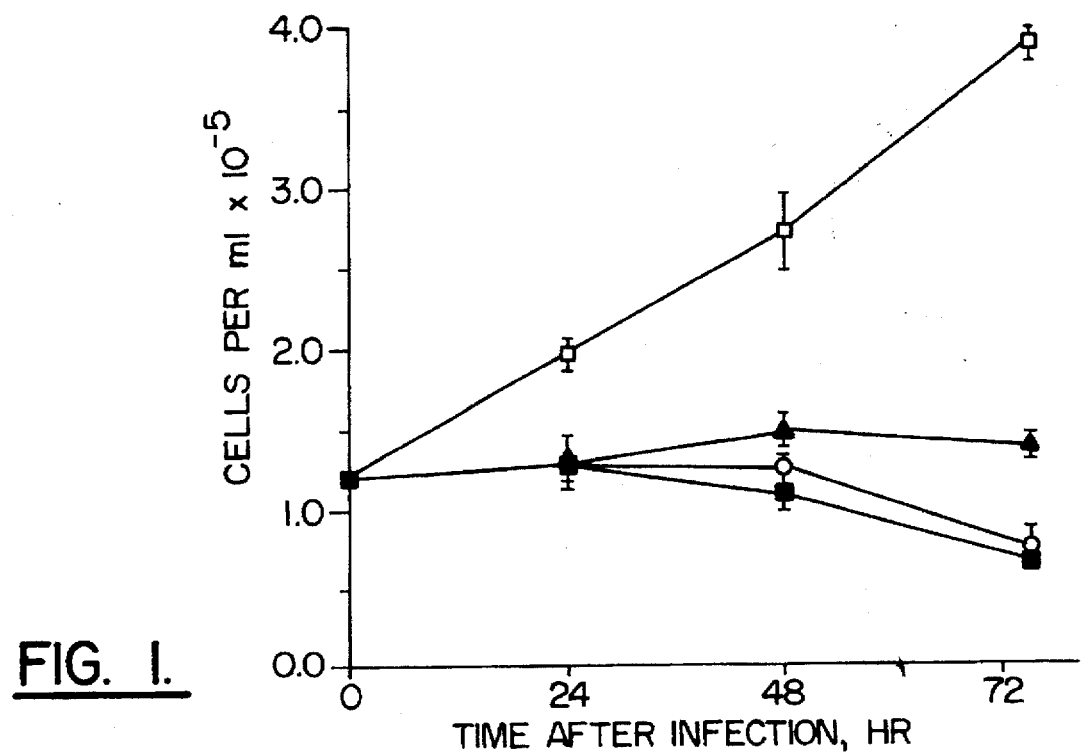
FIG. 1 is a graph showing the effect of infection by various baculoviruses on cell viability of Sf9 cell cultures. Three repetitions were performed for each sample at each time point; error bars indicate SEM. Open circle=BV13T infected Sf9; closed square=BV13.3940 infected Sf9; closed triangle=AcNPV infected Sf9; open square=uninfected Sf9.

Baculoviruses are members of the family Baculoviridae and the genus Baculovirus. The genus comprises three subgroups of viruses: the nuclear polyhedrosis viruses (NPV), the granulosis viruses (GV) and the non-occluded viruses. NPVs include *Autographica californica* NPV (AcNPV), *Heliothis zea* NPV (HzNPV) and *Bombyx mori* NPV (BmNPV). The use of recombinant baculovirus vectors to express foreign proteins in insect cell cultures or larvae is known. See e.g., Luckow & Summers, *Bio/Technology*, 6, 47 (1988); Tomalski & Miller, Nature, 352, 82 (1991). Intentional infection of insect larvae with baculoviruses has been studied for use as a biological control method for insect pests.

Baculoviruses as pest control methods are desirable in that they have limited host ranges, but in general insect death does not occur until several days post-infection. Baculoviruses ingested by insect larvae are dissolved in the midgut, where they release infectious virions which enter gut epithelial cells and other organs and begin to replicate. Tissue damage and eventual death results. Recent studies have addressed decreasing the time required for these viruses to kill insects. Several groups have shown that recombinant baculoviruses expressing insect toxins kill insect larvae more rapidly than wild-type baculoviruses. S. Maeda, et al., Virology 184, 777 (1991); L. Stewart, et al., Nature, 352, 85 (1991); M. Tomalski and L. Miller Nature, 352, 82 (1991).

Two distinct forms of virus are produced by baculovirus infected cells: nonoccluded virus and occluded virus. In the nonoccluded form, nucleocapsids are assembled in the nucleus and acquire an envelope by budding through the plasma membrane to become extracellular virus. In occluded baculoviruses, the virions are embedded in the nucleus in large protein crystals, termed occlusion bodies. Infection with the wild-type *Autographica californica* NPV results in the production of both occluded and non-occluded virions.

The occlusion body is the infectious particle responsible for horizontal transmission of the virus from insect to insect in the wild. The occlusion body apparently provides protection to the virus when outside the host insect. Ingested occlusion bodies dissolve in the midgut of insects, releasing the viral particles for infection. The occlusion body of NPV consists predominantly of a single polypeptide known as polyhedrin. Vlak & Rohrmann, *The Nature of Polyhedrin*, In: *Viral Insecticides for Biological Control*, Academic Press, pp. 489–542 (1985). The polyhedrin promoter is extremely active and polyhedrin is produced in large amounts.

Baculoviruses are useful as recombinant DNA vector systems as a large amount of foreign DNA (up to 20 megadaltons or more) can be inserted. The polyhedrin gene is nonessential for viral replication and foreign DNA may be replaced or inserted into this gene, which is under the control of the active polyhedrin promoter. See U.S. Pat. No. 4,745,051 to Smith (applicants specifically intend the disclosures of all U.S. patents referenced herein to be incorporated by reference herein in their entirety); Miller, 1981, *A Virus Vector for Genetic Engineering in Invertebrates*, In: *Genetic Engineering in the Plant Sciences*, Praeger Publishers, New York, pp. 203–224 (1981); Vlak and Rohrmann, The *Nature of Polyhedrin*, In: *Viral Insecticides for Biological Control*, Academic Press, pp. 489–542 (1985).

Recombinant baculoviruses in which the polyhedrin gene is non-functional are incapable of producing the polyhedrin protein required for the formation of occlusion bodies. U.S. Pat. No. 5,071,748 discloses compositions and methods for co-infecting an insect host with a first baculovirus capable of producing polyhedrin protein and a second recombinant baculovirus containing and expressing a heterologous gene. This results in a mixed baculovirus infection, wherein the heterologous protein is expressed and polyhedral occlusion bodies containing a mixture of nucleocapsids of two genetically distinct baculoviruses are produced. The recombinant baculovirus can thus be transmitted horizontally.

U.S. Pat. No. 4,870,023 discloses a recombinant baculovirus which expresses polyhedrin fusion proteins. The fusion protein includes a foreign amino acid sequence and is capable of crystallizing with other fusion proteins to form recombinant occlusion bodies. The recombinant virus includes the polyhedrin promoter, a nucleotide sequence encoding a portion of the polyhedrin protein that participates in crystallization, and a second nucleotide sequence encoding a foreign protein.

As noted above, the URF13 protein is known to cause sensitivity to T toxin and methomyl when expressed in maize and *E. coli* cells. The T toxin/URF13 interaction results in pore formation in the inner mitochondrial membrane of maize and the plasma membrane of *E. coli*. Levings, *Science*, 250, 942 (1990); Korth et al., *Proc. Natl. Acad. Sci.*, 88, 10865 (1991). We have cloned the T-urf13 gene in a baculovirus expression system and assayed its insecticidal use. In insect cell cultures and insect larvae infected with recombinant baculovirus expressing URF13, URF13 was found to interact with T toxin or methomyl to permeabilize the plasma membranes of insect cells, leading to cell death. Additionally, URF13 was found to have lethal effects when expressed in either invertebrate cell cultures or insect larvae in the absence of T toxin or methomyl. This insecticidal activity makes the recombinant baculovirus useful as a method of controlling agricultural pests when used either alone or in combination with T toxins or methomyl, and useful in agricultural formulations for use pest control.

As used herein, "mitochondrial pore-forming protein" refers to proteins that, alone or upon interaction with a second protein, form a pore or channel in mitochondrial membranes. As used herein, "membrane protein" refers to proteins that are associated with the membrane structures of cells, and encompasses both peripheral membrane proteins and integral membrane proteins.

1. Vector construction

A vector is a replicable DNA construct. Vectors are used herein to express DNA which encodes the 13 kd maize mitochondrial pore-forming protein URF13, or to express DNA which encodes a protein homologous to, and having essentially the same biological properties as, the URF protein. This definition is intended to encompass natural allelic variations in the URF13 sequence. Thus, DNA sequences which hybridize to DNA encoding URF13 and which encode a membrane protein are also an aspect of this invention. Conditions which will permit other DNA sequences which code for expression of a membrane protein to hybridize to DNA encoding T-URF13 can be determined in accordance with known techniques. For example, hybridization of such sequences to DNA encoding URF13 in a standard hybridization assay may be carried out under conditions of reduced stringency, medium stringency or even stringent conditions (e.g., conditions represented by a wash stringency of 35–40% Formamide with 5× Denhardt's solution, 0.5% SDS and 1× SSPE at 37° C.; conditions represented by a wash stringency of 40–45% Formamide with 5× Denhardt's solution, 0.5% SDS and 1× SSPE at 42° C.; and conditions represented by a wash stringency of 50% Formamide with 5× Denhardt's solution, 0.5% SDS and 1× SSPE at 42° C., respectively). See J. Sambrook et al., *Molecular Cloning, A Laboratory Manual* (2d Ed. 1989) (Cold Spring Harbor Laboratory). In general, DNA which codes for membrane proteins and which hybridizes to DNA coding for URF13 will be at least 75% homologous, 85% homologous or even 95% homologous or more with DNA encoding URF13.

Further, DNA sequences which code for polypeptides coded for by DNA encoding URF13, or sequences which hybridize thereto and code for a membrane protein, but which differ in codon sequence from DNA encoding URF13 due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al., at Col. 2, Table 1.

In the expression vector, DNA encoding the URF13 protein is operably linked to suitable control sequences capable of effecting the expression of URF13 protein in a suitable host. DNA regions are operably linked when they are functionally related to each other. For example: a promoter is operably linked to a coding sequence if it controls the transcription of the sequence. Generally, operably linked means contiguous, and, in the case of leader sequences, contiguous and in reading phase.

Baculovirus Vectors: Vectors which may be used in the present invention include baculoviruses such as *Autographica californica* NPV, *Heliothis zea* NPV and *Bombyx mori* NPV. Other baculovirus vectors capable of infecting insect cells and expressing the T-urf13 gene also may be used in the present invention. Baculoviruses which have previously been used as vectors to express foreign gene products include *Autographica californica* NPV (Smith et al., *Mol. Cell. Biol.* 3, 2156 (1983)) and the silkworm virus *Bombyx mori* NPV (Maeda et al., *Nature* 315, 592 (1985)). Infection with a baculovirus normally produces nuclear occlusion bodies consisting of virus particles embedded in polyhedrin protein. Transcription of the polyhedrin gene is driven by an active promoter; the polyhedrin gene product is not essential for viral replication. Construction of expression vectors have consisted of inserting a foreign coding sequence downstream of, and under the control of, the polyhedrin promoter.

Promoters: URF13 expression may be placed under the control of a baculovirus polyhedrin promoter, such as the *Autographica californica* NPV polyhedrin promoter. The T-urf13 gene is downstream of, and under the control of, the promoter.

T-urf13 gene: In general, and as explained in greater detail above, DNA encoding the URF13 protein as used in the present invention includes any DNA encoding a protein functionally equivalent to the URF13 protein. The DNA can be recovered from within the cells of its natural host or it can be synthesized by known procedures. The nucleotide sequence of T-urf13 is known. Dewey, *Cell*, 44, 439 (1986).

2. Formulation and use.

The present invention is useful in controlling insect pests susceptible to infection with the particular recombinant baculovirus used. Compositions of the present invention comprise the baculovirus expression vector as the active agent in any carrier suitable for agricultural use, such as water, organic solvents, and inorganic carriers. The active agent may be in the form of occluded viruses, i.e., viruses in conjunction with the polyhedrin protein. Solid and liquid compositions may be prepared by any conventional procedure which does not affect the viability of the expression vector. Fundamental formulation processes include dissolving, mixing, milling, granulating, dispersing, etc. The present invention encompasses compositions containing the active agent, as described above, in admixture with agriculturally acceptable excipients including vehicles, carriers, binders, UV blockers, adhesives (sticking agents), humectants, thickeners, dispersing agents, preservatives and insect attractants, etc., as are known in the art. Thus compositions of the present invention may, for example, be formulated as a solid comprising the active agent and a finely divided solid carrier. Alternatively, the active agent may be contained in liquid compositions, including dispersions, emulsions and suspensions thereof. Any suitable final form of the composition may be used, including for example, granules, powder, bait pellets (e.g., a solid composition containing the active agent and an insect attractant or food substance), microcapsules, water dispersible granules, emulsions, and emulsifiable concentrates.

The compositions of the present invention may also include conventional insecticidal agents and/or may be applied in conjunction with conventional insecticidal agents. The compositions may also include a second baculovirus capable of producing polyhedrin protein (see U.S. Pat. No. 5,071,748).

Examples of adjuvants or carriers suitable for use with the present invention include talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour, and lignin.

The present method is useful in controlling agricultural insect pests susceptible to baculoviral infections, an is particularly useful in controlling insect pests belonging to the Order Lepidoptera. As used herein, the term insect includes both larval and adult forms. The recombinant baculovirus may be applied to the subject agricultural field in any manner which results in the recombinant baculovirus coming in contact with the feeding insects to be controlled, or with the particular plant part to be consumed by the insect. For example, in targetting surface leaf-feeding insects, a composition containing the baculovirus would be formulated to adhere to leaves (e.g., formulated with sticking agents or adherents) and would be applied in a manner to contact the leaves of the plants (e.g., spraying or dusting). The recombinant baculovirus is applied in an amount sufficient to result in baculovirus infection of the target insect when ingested. One or more applications may be used. The method of the present invention may be used in addition to or in conjunction with other control measures.

Suitable application methods include, but are not limited to, methods such as dusting or spraying. The active agent can be applied as an aerosol, e.g., by dispersal in the air by means of a compressed gas such as dichlorodifluoromethane or trichlorofluoromethane. The active agent may be applied alone or in combination with inert solids such as a dust or suspended in a liquid solution such as an organic solvent or an aqueous solution; a surfactant may be added to the solution. Compositions may be applied dry or in the form of a suspension, emulsion or foam. The active agent is applied to the target insect, areas containing the target insect or parts of plants to be consumed by the target insect, including but not limited to vegetation, fruit, seed, soil or aquatic locales.

The present invention is explained in greater detail in the following non-limiting examples. These examples are provided so that the invention can be more completely understood and are not to be construed as limiting the invention. Amino acid sequences disclosed herein are presented in the amino to carboxyl direction, from left to right. The amino and carboxyl groups are not presented in the sequence. Nucleotide sequences are presented herein by single strand only, in the 5' to 3' direction, from left to right. Nucleic and amino acid residues are identified by accepted one or three letter abbreviations (see, e.g., Genes and Genomes, Singer & Berg (Eds.) University Science Books, Mill Valley, Calif., 1991 at pp. 37, 60).

In the examples, AcNPV means *Autographica californica* nuclear polyhedrosis virus; MAb means monoclonal antibody; FDA means fluorescein diacetate; EGS means ethylene glycolbis (succinimidylsuccinate); SEM means standard error of the mean; EDTA means edetic acid; PBS means phosphate buffered saline; g means gravity; mg means milligram; μg means microgram; ng means nanogram; ml means milliliter; μl means microliter; M means molar; mM means millmolar; nm means nanometer; ° C. means degrees Centigrade; and Sf means *Spodoptera frugiperda* (fall armyworm).

EXAMPLE 1

Materials and Methods

T-urf13 Cloning. DNA manipulations were carried out as described previously (J. Sambrook, et al., *Molecular Clon-* ing: A Laboratory Manual (Cold Spring Harbor Lab., Plainview, N.Y.) (1989)). A 2-kbp HindIII fragment from cms-T maize mitochondrial DNA (R. Dewey, et al., Science 239, 293 (1988)) was ligated into pBluescript KS-(Stratagene), and a BamHI restriction site was created just upstream of the T-urf13 open reading frame using site-directed mutagenesis (T. Kunkel, Proc. Natl. Acad. Sci. USA 82, 488 (1985)). To create a T-toxin-insensitive form of URF13, nucleotides encoding residues 39 and 40 of URF13 were altered to codons for glycine, from 5'-GAT-GAT-3' to 5'-GGT-GGT-3'. Kunkel Proc. Natl. Acad. Sci. USA, 82, 488 (1985). The alteration of residue 40 has no known effect on T toxin or methomyl sensitivity conferred by URF13 in E. coli. The entire T-urf13 open reading frame, included in 511-bp BamHI/BglII fragments, was ligated into the BamHi site of pAcYMI (provided by D. H. L. Bishop, Natural Environment Research Council Institute of Virology, Oxford) (Y. Matsuura, et al., J. Gen. Virol. 68, 1233 (1987)) to create constructs with the wild-type form of T-urf13 (pAc13T) and the mutagenized form (pAc13.3940). In each case the T-urf13 gene was downstream of the polyhedrin promoter of AcNPV. DNA sequencing (F. Sanger, et al., Proc. Natl. Acad. Sci USA 74, 5463 (1977)) confirmed that the 5' insertion point was 5' . . . AAATA'CGGATC-CAATG . . . 3', where A' is a remnant of the polyhedrin protein initiation codon, and ATG is the first codon of the T-urf13 gene.

For expression in E. coli, the entire open reading frame of the T-URF13 gene was ligated into an inducible expression vector, pKK223 (Pharmacia LKB); this construct has been designated pKK13T (Carl J. Braun, personal communication).

Baculovirus, Cell Culture, and Larvae Handling. pAc13T and pac13.3940 were introduced along with AcNPV DNA (provided by M. D. Summers, Texas A & M University) into Sf21 cells via liposome-mediated transfection (P. Hartig, et al, BioTechniques 11, 310 (1991)) or calcium phosphate precipitation (M. Summers & G. Smith, A Manual of Methods for Baculovirus Vectors and Insect Cell Culture Procedures (Texas Agric. Exp. Stn., TX, Bull. No. 1555 (1988)). Recombinant viruses were selected by visual screening of cell monolayers for viral plaques not producing the polyhedrin protein (occlusion-negative) as previously described (M. Summers & G. Smith, A Manual of Methods for Baculovirus Vectors and Insect Cell Culture Procedures (Texas Agric. Exp. Stn., TX, Bull. No. 1555 (1988)), except that 0.1% neutral red was added to plates. Recombinant baculoviruses expressing β-galactosidase (BV βgal) were isolated using the same procedures (pAc360β-gal provided by M. D. Summers).

Isolation of AcNPV DNA, infections, and maintenance of cell cultures were performed as previously described (M. Summers & G. Smith, A Manual of Methods for Baculovirus Vectors and Insect Cell Culture Procedures (Texas Agric. Exp. Stn., TX, Bull. No. 1555 (1988)). Viral infections were made with a multiplicity of infection of 5–10. All experiments with infected cells were carried out at 48 hours post-infection unless indicated otherwise. Antibiotics (gentamicin sulfate (50 µg/ml) and amphotericin B (2.5 µg/ml)) were used only during transfections and selection of recombinant viruses; antibiotics were not present during studies of URF13 function or toxicity. Trichoplusia ni (cabbage looper) larvae were maintained at 27° C. as described (R. Roe, et al Ann. Entomol. Soc. Am. 75, 421 (1982)).

Anti-URF13 Antibodies and Protein Handling. Production and characterization of anti-URF13 monoclonal antibody (mAb) have been described (K. Korth, et al Proc. Natl. Acad. Sci USA 88 10865 (1991)). SDS/PAGE was carried out on 16.5% acrylamide/Tris-tricine gels as described (H. Schägger & G. von Jagow Anal. Biochem. 166 368 (1987)). Immunoblots were prepared as described (E. Harlow & D. Lane Antibodies: A Laboratory Manual (Cold Spring Harbor Lab., Plainview, N.Y. (1988)) using a luminescent detection system (ECL; Amersham). Cross-linking was carried out with ethylene glycolbis(succinimidysuccinate) (EGS) (Pierce) on whole cells (K. Korth, et al Proc. Natl. Acad. Sci USA 88 10865 (1991)).

For membrane preparation, Sf9 cells were suspended in phosphate-buffered saline (PBS; 10 mM $Na_2PO_4$/1.8 mM $KH_2PO_4$/0.8% NaCl/0.14% KCl, pH 7.2), 5 mM EDTA, 50 µg of phenylmethylsulfonyl fluoride per ml, 2 mg of leupeptin per ml, and 1 mg of pepstatin per ml. The suspension was sonicated 4×20 seconds with a Fisher sonic dismembrator model 300 microtip at 35% power. Remaining whole cells and debris were removed by centrifugation at 8000× g, and membranes were separated from soluble fractions by centrifugation at 150,000× g. T. ni larvae were homogenized with a TEFLON (TM) pestle in the same buffer as above with 0.01% phenylthiourea. Larval cell membranes were prepared the same as for Sf9 cultures, except that the 8000× g spin was carried out three times.

URF13 Functional Studies. Fluorescein diacetate (FDA) in acetone (1 mg/ml) was diluted 1:4000 in PBS and added to cell suspensions at 1:3. Cells were suspended in PBS, incubated for 5 minutes with or without 8 mM methomyl (provided by DuPont) or with or without 780 ng of T toxin per ml (gift of H. W. Knoche and S. J. Danko, University of Nebraska) and then stained with FDA. Fluorescent cells were visualized on a Nikon inverted microscope with a B-2A filter (excitation at 450–490 nm) and counted on a Neubauer hemacytometer. Light absorbance of Sf9 cells was measured over time at 520 nm with constant stirring. LANNATE (TM), 12.3 µl (1.3M methomyl), was added (to 8 mM) to 2-ml suspensions of cells ($2\times10^7$ cells per ml) in PBS. Alternatively T toxin was added to 780 ng/ml to identical cell suspensions.

URF13 Toxicity Studies. Sf9 cells were counted on a Neubauer hemacytometer. Viable cells were identified by their failure to take up trypan blue, 0.04% final concentration in PBS.

Third to fourth instar T. ni larvae were injected with about $2\times10^4$ plaque-forming units in 1 µl of complete medium. Those larvae not surviving the injection procedure were removed from the study. Larvae were counted as dead when they failed to respond to slight prodding.

EXAMPLE 2

Expression of URF13 in Insect Cell Culture

Baculoviruses BV13T and BV13.3940, which contain T-urf13 genes, were created via homologous recombination between pAc13T or pac13.3940, respectively, and wild-type AcNPV DNA was created by cotransfection in insect cell cultures. BV13.3940 contains site-directed mutations at positions encoding amino acid residues 39 and 40, so that it is predicted to encode:

instead of the wild-type:
Mutations at residue 39 render T-urf13 incapable of conferring T toxin or methomyl sensitivity to *E. coil* (C. Braun, et al *Proc. Natl. Acad. Sci. USA* 86, 4435 (1989)).

BV13T- and BV13.3940-infected Sf9 cell extracts and cell membranes contained novel proteins of approximately 13 and 11 kDa compared with uninfected or AcNPV-infected cells, as determined by Coomassie blue staining of SDS/PAGE gels (data not shown). Scanning densitometry of infected cell extract lanes indicated that these two proteins together made up ≈2% of the total stainable protein.

Infecting Sf9 cultures with viral isolates BV13T or BV13.3940 produced two membrane-bound proteins that were immunoreactive with a MAb specific for the carboxyl terminus (mAb-C) of URF13 (data not shown). The higher molecular mass, immunoreactive protein in this blot migrated on SDS/PAGE gels at a position identical to that of URF13 from cms-T mitochondria (data not shown). Antibodies that recognize URF13 did not react with proteins from uninfected cells, cells infected with the wild-type AcNPV, or the soluble fraction obtained from BV13T- or BV13.3940-infected cells (data not shown). Neither of the two URF13 species produced in infected cells could be removed from membranes by treatment with 0.1 $MNa_2CO_3$ (data not shown), indicating that they are both integral membrane proteins. Differential gel migration predicted that the lower molecular mass protein is about 2kDa smaller than full-length URF13 (13 kDa). The smaller protein probably lacks amino acid residues largely from the amino terminus because it is reactive with the carboxyl-specific MAb-C. This same protein expression pattern was observed after infection with each of eight independent viral isolates.

URF13 forms multimeric structures in insect cell membranes, which have also been shown in membranes from cms-T mitochondria and *E. coli* cells expressing this protein (K. Korth, et al., *Proc. Natl. Acad. Sci USA* 88, 10865 (1991)). Treating BV13T- and BV13-3940-infected cells with a lysine-specific, hydrophobic, bifunctional crosslinker, EGS, gave rise to MAb-C reactive proteins that migrated on SDS/PAGE gels at positions predicted for URF13 homomultimers (data not shown). The presence of multiple bands migrating near the putative dimers, trimers, and tetramers indicated that the smaller URF13 species produced in Sf9 cells also participates in forming multimers. The predominant multimeric URF13 species produced in Sf9 cells co-migrated with MAb-C immunoreactive proteins from cross-linker-treated *E. coli* expressing the T-urf13 gene product (data not shown). A small amount of putative dimer was present in untreated *E. coli* and cms-T mitochondria (data not shown); this form of URF13 often appears in protein immunoblots containing URF13 (K. Korth et al., *Proc. Natl. Acad. Sci USA* 88, 10865 (1991)) (E. Lin et al., *Plant Physiol.* 95, 861 (1991)). Immunofluorescence studies of fixed Sf9 cells using MAb-C as a probe indicated that URF13 is found throughout BV13T-infected cells, whereas virtually no antibody binding occurred in cells infected with another recombinant virus, BVβgal (data not shown). In cms-T maize, URF13 is synthesized in the mitochondrial matrix and integrated into the inner mitochondrial membrane. Because mitochondrial targeting sequences were not included in BV13T or BV13.3940, URF13 was not expected to associate specifically with mitochondria in Sf9 cells.

TABLE 1

Effect of methomyl (8 mM) or T toxin (780 ng/ml) on the integrity of Sf9 plasma membranes as measured by the number of virus-infected cells stained with a vital stain, FDA

| VIRUS | TREATMENT | CELLS PER ML × $10^5$* | Δ%† |
|---|---|---|---|
| BV13T | None | 3.00 ± 0.205 | — |
| | Methomyl | 0.675 ± 0.063 | 77.5 |
| | T toxin | 0.725 ± 0.063 | 75.8 |
| BVβgal | None | 3.10 ± 0.325 | — |
| | Methomyl | 3.20 ± 0.295 | −3.2 |
| | T toxin | 2.95 ± 0.120 | 4.8 |
| AcNPV | None | 3.65 ± 0.235 | — |
| | Methomyl | 3.58 ± 0.110 | 1.9 |
| | T toxin | 3.60 ± 0.240 | 1.4 |
| BV13.3940 | None | 3.10 ± 0.155 | — |
| | Methomyl | 2.95 ± 0.065 | 4.8 |
| | T toxin | 2.93 ± 0.125 | 5.5 |

*Mean (x) ± SEM of four treatments
†Δ% = (1 − x after treatment/x with no treatment) × 100.

EXAMPLE 3

Fungal Toxin and Methomyl Sensitivity in Insect Cells

URF13 interacts with T toxin or methomyl to permeabilize membranes in maize mitochondria and *E. coli* cells. Sf9 cells expressing wild-type URF13 also showed sensitivity to T toxin and methomyl. Treating BV13T-infected cells with methomyl or T toxin resulted in a >75% reduction in the number of cells that could be observed with the vital stain FDA (Table 1). The fluorescent, polar product of hydrolyzed FDA is retained only in cells with intact plasma membranes, whereas dead or dying cells rapidly leak the dye (B. Rotman and B. Papermaster, *Proc. Natl. Acad. Sci. USA* 55, 134 (1966)). Table 1 shows that a short incubation with T toxin or methomyl reduces the number of stained cells among cells producing wild-type URF13, probably by its effects on plasma membranes; in contrast, cells infected with BV13.3940, AcNPV, or BVβgal are virtually unaffected.

Suspensions of BV13T-infected SF9 cells expressing wild-type URF13 showed a significant decrease over time in light absorbance at 520 nm after adding methomyl in 9 mM (data not shown). No such change was observed in cells infected with BV13.3940 or Bvβgal. The decrease in light scattering indicates a loss of membrane integrity, which is thought to be due to cell swelling. This technique has been used to show T-toxin sensitivity in cms-T mitochondria (R. Miller and D. Koeppe, Science 173, 67 (1971)), (B. Gengenbach, et al., *Can. J. Bot.* 51, 2119 (1973)) and *E. coli* spheroplasts expressing URF13 (R. Dewey, et al., *Science* 239, 293 (1988)). This result provides further evidence that URF13 permeabilizes plasma membranes of methomyl-treated Sf9 cells. A similar decrease in absorbance was seen in Sf9 cells expressing wild-type URF13 after adding T toxin; no changes were observed in BV13.3940-infected cells or control group cells (data not shown).

EXAMPLE 4

Toxicity of URF13 in Cell Cultures and Insect Larvae

We measured the toxic effects of URF13 production in cell cultures by counting live cells at time intervals after infection. Baculoviral infection causes a rapid cessation of growth of insect cell cultures (L. Volkman, et al., *J. Virol.* 19, 820 (1976)). Cells infected with BV13T or BV13.3940 died at a significantly faster rate than cells infected with either AcNPV (FIG. 1) or BV βgal (data not shown). The presence of 2 mM methomyl in these cultures did not cause a detectable difference, compared to cultures grown without methomyl, in the numbers of live cells over time (data not shown). In cultures grown with methomyl, however, the abundance of URF13 was significantly diminished, and the smaller URF13 species was virtually absent (data not shown). The expression pattern of URF13 in BV13.3940-infected cultures was not affected by 2 mM methomyl.

Figure 2:
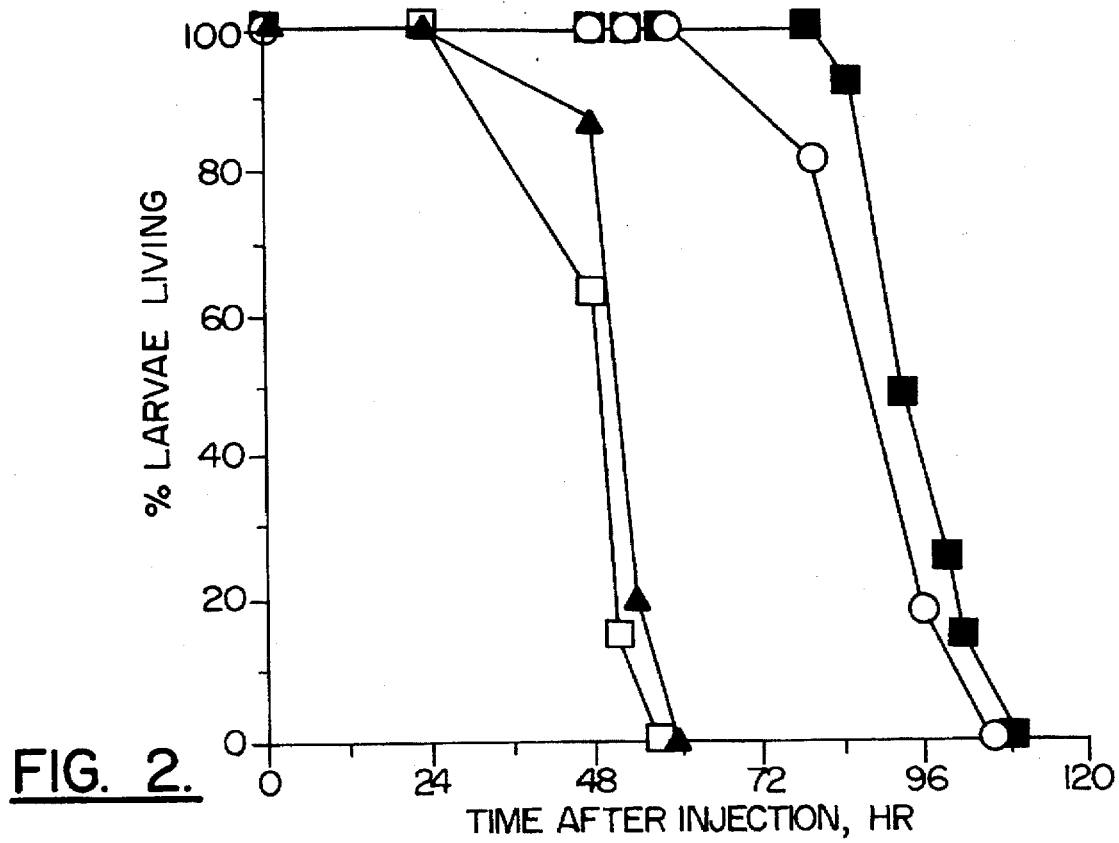
FIG. 2 is a graph showing the effect of injection of various baculoviruses on the viability of third to fourth instar *T. ni* larvae, as measured in the percentage of larvae surviving over time. Open square=BV13T; open circle=BVβgal; closed square=AcNPV; closed triangle=BV13.3940.

These results show that URF13 has lethal effects when produced in insect larvae in the absence of T toxin or methomyl (FIG. 2). One hundred percent of third to fourth instar *T. ni* larvae injected with BV13T or BV13.3940 were dead within 60 hours after injection. Larvae injected with either AcNPV or BVβgal lived up to 106 hours or 100 hours after injection, respectively. Larvae injected with complete medium survived normally and underwent pupation (data not shown). URF13 apparently undergoes specific proteolysis in *T. ni* larvae. As in Sf9 cultures, a MAb-C-reactive protein of the same size as wild-type URF13 was localized in BV13T- and BV13.3940-infected larval membranes. Additional proteins of lower molecular mass were also recognized by MAb-C (data not shown). Immunoreactive URF13 was detectable in larval samples beginning at 36 hour post-injection (data not shown).

The foregoing examples are illustrative of the present invention, and are not to be construed as limiting thereof. The invention is defined by the following claims, with equivalents of the claims to be included therein.

That which is claimed is:

1. A method of reducing the population of an insect in an agricultural field comprising applying to the field a recombinant baculovirus capable of producing polyhedrin protein and which is able to infect the insect, said recombinant baculovirus applied in an amount effective to reduce the population of the insect, and said baculovirus containing and expressing heterologous DNA selected from the group consisting of:

(a) isolated DNA which encodes the maize mitochondrial pore-forming protein URF13;
   (b) isolated DNA which hybridizes to isolated DNA of (a) above under conditions represented by a wash stringency of 0.3M NaCl, 0.03M sodium citrate, and 0.1% SDS at 60° C., and which encodes a membrane protein; and
   (c) isolated DNA differing from the isolated DNAs of (a) and (b) above in codon sequence due to the degeneracy of the genetic code, and which encodes the protein encoded by DNA of (a) or (b) above.

2. The method of claim 1, wherein said heterologous DNA is operatively linked with a promoter operable in insect cells.

3. The method of claim 2, wherein said promoter is a baculovirus polyhedrin promoter.

4. The method of claim 2, wherein said promoter is the polyhedrin promoter of *Autographica californica* nuclear polyhedrosis virus.

5. The method of claim 1, wherein said baculovirus infects lepidopteran larvae present in the field.

6. The method of claim 1, wherein said baculovirus is selected from the group consisting of *Autographica californica* nuclear polyhedrosis virus, *Heliothis zea* nuclear polyhedrosis virus and *Bombyx mori* nuclear polyhedrosis virus.

7. The method of claim 1, wherein said recombinant baculovirus produces methomyl sensitivity in an insect infected with said baculovirus.

8. The method of claim 1, wherein said recombinant baculovirus produces T toxin sensitivity in an insect infected with said baculovirus.

9. The method of claim 7, further comprising the step of applying methomyl to the field in an amount effective to kill baculovirus-infected larvae in the field.

10. The method of claim 8, further comprising the step of applying T toxin to the field in an amount effective to kill baculovirus-infected larvae in the field.

11. The method of claim 10, wherein said T toxin is selected from the group consisting of *Bipolaris maydis* race T (BmT) toxin and *Phyllosticta maydis* (Pm) toxin.

12. The method of claim 1, wherein said insect belongs to the Order Lepidoptera.

13. The method of claim 1, wherein said insect belongs to a genus selected from the group consisting of Spodoptera and Trichoplusia.

14. The method of claim 1, wherein said insect is *Spodoptera frugiperda*.

15. The method of claim 1, wherein said insect is *Trichoplusia ni*.

16. The method of claim 1, wherein said baculovirus is applied to said field in a form selected from the group consisting of liquid suspensions, emulsions, aerosols, powdered solids, granulated solids, bait pellets, foams, microcapsules, and water dispersible granules.

17. A composition for reducing the population of an insect in an agricultural field, comprising an effective insect-population reducing amount of a recombinant baculovirus capable of producing a polyhedrin protein, said baculovirus capable of infecting the insect and containing and expressing heterologous DNA selected from the group consisting of:

(a) isolated DNA which encodes the maize mitochondrial pore-forming protein URF13;
   (b) isolated DNA which hybridizes to isolated DNA of (a) above under conditions represented by a wash stringency of 0.3M NaCl, 0.03M sodium citrate, and 0.1% SDS at 60° C., and which encodes a membrane protein; and
   (c) isolated DNA differing from the isolated DNAs of (a) and (b) above in codon sequence due to the degeneracy of the genetic code, and which encodes the protein encoded by DNA of (a) or (b) above.

18. The composition of claim 17, further comprising a suitable agricultural carrier.

19. The composition of claim 18, wherein said agricultural carrier is an oil.

20. The composition of claim 18, wherein said agricultural carrier is an emulsion.

21. The composition of claim 18, wherein said agricultural carrier is selected from the group consisting of talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour, and lignin.

22. The composition of claim 17, further comprising a sticking agent.

23. The composition of claim 17, further comprising an insect attractant.

24. A method of reducing the population of an insect in an agricultural field comprising applying to the field a recombinant nuclear polyhedrosis baculovirus which is able to infect the insect, said recombinant nuclear polyhedrosis baculovirus applied in an amount effective to reduce the population of the insect, and said recombinant nuclear polyhedrosis baculovirus containing and expressing heterologous DNA selected from the group consisting of:

(a) isolated DNA which encodes the maize mitochondrial pore-forming protein URF13;

(b) isolated DNA which hybridizes to isolated DNA of (a) above under conditions represented by a wash stringency of 0.3M NaCl, 0.03M sodium citrate, and 0.1% SDS at 60° C., and which encodes a membrane protein; and (c) isolated DNA differing from the isolated DNAs of (a) and (b) above in codon sequence due to the degeneracy of the genetic code, and which encodes the protein encoded by DNA of (a) or (b) above.

25. The method of claim 24, wherein said nuclear polyhedrosis baculovirus infects lepidopteran larvae present in the field.

26. The method of claim 24, wherein said recombinant nuclear polyhedrosis baculovirus produces methomyl sensitivity in an insect infected with said baculovirus.

27. The method of claim 24, wherein said recombinant nuclear polyhedrosis baculovirus produces T toxin sensitivity in an insect infected with said baculovirus.

28. The method of claim 26, further comprising the step of applying methomyl to the field in an amount effective to kill recombinant nuclear polyhedrosis baculovirus-infected larvae in the field.

29. The method of claim 27, further comprising the step of applying T toxin to the field in an amount effective to kill recombinant nuclear polyhedrosis baculovirus-infected larvae in the field.

30. The method of claim 24, wherein said insect belongs to the Order Lepidoptera.

31. The method of claim 24, wherein said insect belongs to a genus selected from the group consisting of Spodoptera and Trichoplusia.

32. The method of claim 24, wherein said recombinant nuclear polyhedrosis baculovirus is applied to said field in a form selected from the group consisting of liquid suspensions, emulsions, aerosols, powdered solids, granulated solids, bait pellets, foams, microcapsules, and water dispersible granules.

33. The composition of claim 17, wherein said recombinant baculovirus is selected from the group consisting of *Autographa californica* nuclear polyhedrosis virus, *Heliothis zea* nuclear polyhedrosis virus and *Bombyx mori* nuclear polyhedrosis virus.

34. The composition of claim 17, wherein said recombinant baculovirus is *Autographa californica*.

* * * * *